United States Patent [19]

Ekwall

[11] Patent Number: 5,423,866
[45] Date of Patent: Jun. 13, 1995

[54] CONSTANT CHARGE PACEMAKER

[75] Inventor: Christer Ekwall, Spanga, Sweden

[73] Assignee: Siemens Aktiengesellschaft, Munich, Germany

[21] Appl. No.: 118,587

[22] Filed: Sep. 10, 1993

[30] Foreign Application Priority Data

Sep. 18, 1992 [EP] European Pat. Off. ............ 92116036

[51] Int. Cl.⁶ .............................................. A61N 5/01
[52] U.S. Cl. ........................................ 607/11; 607/12
[58] Field of Search .................... 607/2, 4, 5, 7, 9, 11, 607/65, 12

[56] References Cited

U.S. PATENT DOCUMENTS

| | | |
|---|---|---|
| 4,050,004 | 9/1977 | Greatbatch . |
| 4,321,928 | 3/1982 | Elmqvist . |
| 4,494,544 | 1/1985 | Lambert . |
| 5,178,140 | 1/1993 | Ibrahim ................................. 607/4 |
| 5,233,982 | 8/1993 | Kohl ..................................... 607/65 |

OTHER PUBLICATIONS

"The Mythology of Threshold Variations as a Function of Electrode Surface Area," Stokes et al. PACE, vol. 14, Nov. 1991, Part II, pp. 1748–1751.

*Primary Examiner*—William E. Kamm
*Assistant Examiner*—Scott M. Getzow
*Attorney, Agent, or Firm*—Hill, Steadman & Simpson

[57] ABSTRACT

A pacemaker has a pulse source for delivering heart stimulation pulses to at least one heart stimulation electrode which includes a source for charging a charge storage element with a prescribed amount of charge for each heart stimulus. The charge storage element is then caused to discharge a predetermined amount of charge through the stimulation electrode to form a heart stimulation pulse.

8 Claims, 2 Drawing Sheets

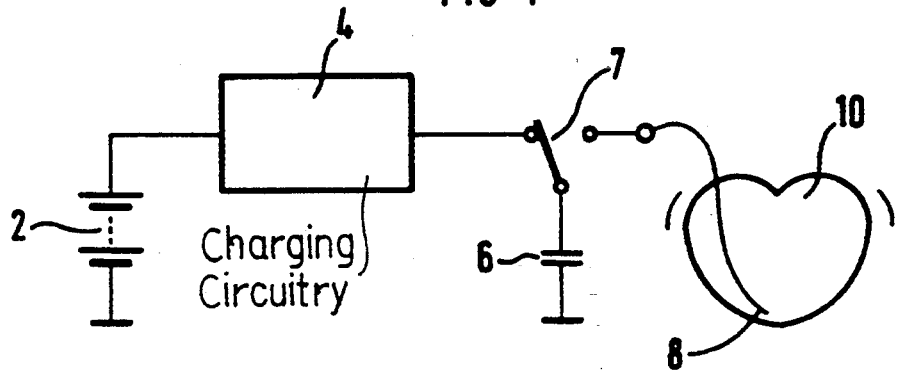
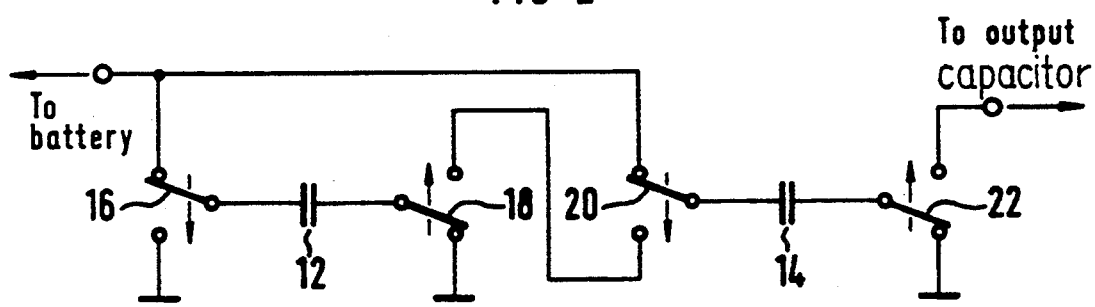
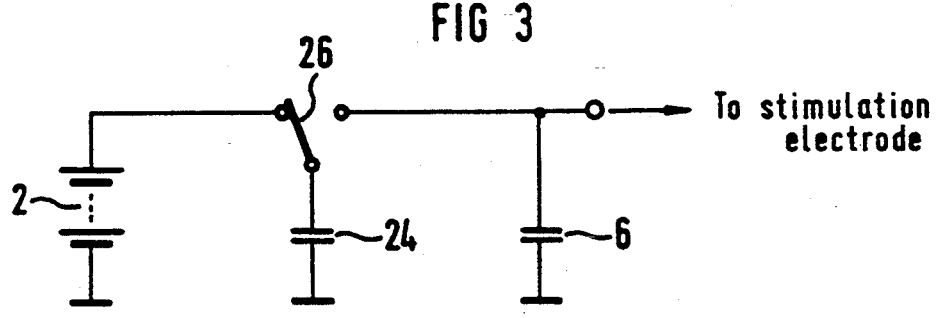

CONSTANT CHARGE PACEMAKER

BACKGROUND OF THE INVENTION

1. Field of the Invention

The present invention relates to a pacemaker having a pulse source for delivering heart stimulation pulses to at least one heart stimulation electrode.

2. Description of the Prior Art

In biomedical therapy of heart diseases electric stimulation of the tissue is often utilized. In the presence of normal, spontaneous activity of the heart, stimulation is inhibited or synchronized to the sensed natural event.

It is important that contraction of the heart is achieved as a result of stimulation, so-called stimulation capture. When a stimulation apparatus is implanted tile minimum stimulation voltage for capture is normally determined. It is well-known that the threshold value of stimulation capture is initially temporarily increased to a maximum over a number of weeks. It is also well-known that this threshold value will vary with the passage of time. Because of these effects the stimulation level must be set rather high to insure stimulation capture. Often a stimulation voltage of twice or more the measured threshold value is selected as a standard procedure. As a result the current consumption is increased with a factor of four above the measured threshold value for stimulation capture, with a shortened longevity of the stimulator as a consequence. This is a serious inconvenience and there is continuing need within this technical field to reduce the necessary stimulation energy and to lengthen the intervals between replacement surgeries.

A larger contact area with the tissue of the stimulation electrode normally results in a more stable stimulation threshold, whereas a smaller contact area of the stimulation electrode, below about 3 mm$^2$, causes larger spreads and variations in the threshold value, cf. eg. Stokes et al, The Mythology of Threshold Variations as a Function of Electrode Surface Area, PACE, Volume 14, November 1991, Part II, pp. 1748–1751. A small electrode contact area, however, has a higher electrical contact impedance and consequently losses of energy in electric wires and output switches are reduced. Further, the current density seems to be one factor of major importance for obtaining stimulation capture and a high current density is obtained at a lower stimulation voltage with a small electrode contact area with the tissue.

Fibrotic tissue growth and fat-cells will increase the contact impedance between the electrode and surrounding tissue and result in large local variations. This effect causes problems when using small electrode surfaces, but is equalized over larger electrode surfaces. Higher energies will also overcome this difficulty; a higher energy can stimulate cells located a distance away and will thus "bridge over" a nonconductive layer.

Implantation of a pacemaker is normally followed-up by monitoring the value of the stimulation threshold, measured in voltage peak amplitude, and stimulation impedance variations, as seen from the pacemaker. This impedance is normally of the order of 500 ohm. Larger deviations in these values indicate inappropriate pacing conditions.

Since the use of small stimulation electrodes has indisputable advantages, the interest in such electrodes has increased. Stimulation pulses are currently determined by voltage amplitude and duration, sometimes by stimulation current and duration. If the contact impedance then is increased, which normally occurs when reducing the contact area, the stimulation energy is, however, decreased with an obvious risk for loss of capture.

SUMMARY OF THE INVENTION

An object of the present invention is to solve the problem of loss of stimulation capture because of high or unstable contact impedances when using pacemakers with small lead area electrodes.

The above object is achieved in accordance with the principles of the present invention in a cardiac pacemaker having a pulse source for delivering heart stimulation pulses to cardiac tissue via at least one stimulation electrode, the pulse source including a source for charging a charge storage element with a prescribed amount of charge for each heart stimulus, the charge storage element being operated to discharge a predetermined amount of charge through the stimulation electrode to form a heart stimulation pulse.

According to the present invention a pacemaker is disclosed with which the problem of loss of stimulation capture at high or unstable contact impedances is overcome by delivering a predetermined amount of stimulation charge, instead of using a predetermined stimulation voltage. When stimulating with a predetermined, programmed amount of charge the output voltage will automatically be increased if the contact impedance is increased. Thus with the pacemaker according to the invention the problem of e.g. decreased conductivity at the edge of an electrode with small surface caused by fat-cells or fibrotic growth is eliminated. If a loss of capture should be detected when using a pacemaker according to the invention the predetermined stimulation charge will be increased.

According to an embodiment of the pacemaker of the invention, at least two capacitors are charged in parallel across the battery and then discharged in series to the charge storage means. In this way a capacitive voltage multiplier is provided which permits output voltages to be obtained which are several times higher than the voltage of the battery.

According to a further embodiment of the pacemaker of the invention, the charge storage means is charged by a so-called charge pump. To obtain a constant stimulation charge it is then sufficient to have a charge pump with a maximum output voltage of two times the stimulation output voltage. The amount of charge delivered to the output capacitor is proportional to the time the charge pump is in operation. To select a certain output stimulation charge the time of operation for the charge pump after a stimulation is fixed. In a situation where the energy drawn from the energy source of the pacemaker is primarily used for heart stimulation, i.e. losses are negligible, a constant amount of energy supplied per stimulus, would result in a constant stimulation charge.

According to another embodiment of the pacemaker of the invention, the charge storage means is a high inductance coil which discharges stored magnetic energy directly through the electrode as a stimulation pulse. The prescribed amount of charge will then be discharged and the output voltage will be automatically adapted to necessary values. Thus if the transition impedance is increased the voltage will also increase such that a sufficient current for the prescribed amount of charge is delivered.

According to a further embodiment of the pacemaker of the invention, the charging source is a battery charging a coil, which in turn charges the charge storage means. In such an embodiment charging losses are reduced to a minimum.

According to another embodiment of the pacemaker of the invention, the charge storage means is an output capacitor and a comparator is provided for comparing the voltage of this output capacitor with a predetermined security level during the charging operation. The comparator stops the charging if the voltage of the capacitor should reach this security level.

DESCRIPTION OF THE DRAWINGS

FIG. I is a schematic block diagram illustrating the principles of one embodiment of the pacemaker according to the invention.

FIG. 2 shows how charge storage means of the pacemaker according to the invention can be charged to a voltage exceeding the voltage of the battery.

FIG. 3 illustrates the principle of charge pumping used in one embodiment of the pacemaker according to the invention.

DESCRIPTION OF THE PREFERRED EMBODIMENTS

Figure 4:
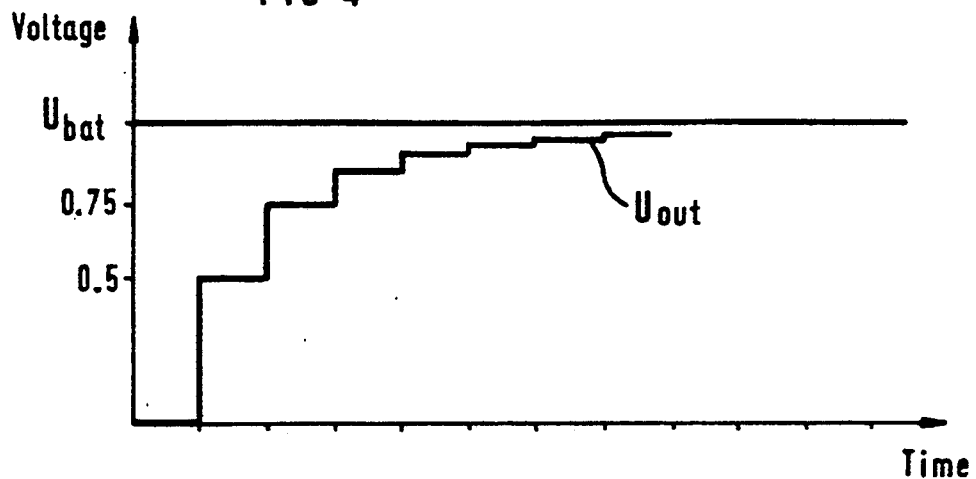
FIG. 4 illustrates how the output voltage of the circuit in FIG. 3 is stepwise increased during the charging procedure.

FIG. 1 illustrates the basic layout of a pulse source of the pacemaker according to the invention. The pulse source includes a charging source having a battery 2 and charging circuitry 4 for charging a charge storage means in the form of an output capacitor 6. When the capacitor 6 is charged to a predetermined level, it is discharged by a switch 7 through a stimulation electrode 8 implanted in a heart 10. The voltage of the battery 2 is normally about 3 volts. To be able to obtain higher stimulation voltages the charging circuitry 4 can include a capacitive voltage multiplier or "charge pump" of the type illustrated in FIG.2.

During charging the capacitors 12 and 14 are connected in parallel to the battery, the switches 16, 18, 20 and 22 being in the position shown in FIG. 2. The switches 16, 18, 20 and 22 are then switched in the directions of the arrows into their other positions in which the capacitors 12 and 14 are connected in series for discharge to the output capacitor 6. Thus the output capacitor 6 will be charged from the capacitors 12 and 14 with a voltage which is twice the battery voltage. Of course the circuit of FIG. 2 can include more than two capacitors, thus realizing a corresponding higher voltage multiplication.

As an alternative the output capacitor 6 can be charged by a charge pump the principle of which is illustrated in FIGS. 3 and 4.

In this latter case the charging e circuitry 4 includes a capacitor 24 which is first connected to the battery 2 through the switch 26. Thus capacitor 24 is first charged to the voltage $U_{bat}$ of the battery 2. The position of the switch 26 is then changed and the output capacitor 6 is charged from the capacitor 24 to the voltage $U_{bat}/2$, the two capacitors 6 and 24 then having equal voltage. The switch 26 is then switched to its first position again and the capacitor 24 is again charged to the voltage $U_{bat}$. The switch 26 is switched to its second position to discharge the capacitor 24 to the capacitor 6 until the voltages of the two capacitors are the same and equal to 0.75 $U_{bat}$.

The capacitor 24 is again charged to voltage $U_{bat}$, again connected to the capacitor to again charge this capacitor until the voltage of the two capacitors are equal to 0.875 $U_{bat}$, etc. until the output capacitor 6 has been charged to desired level.

This gradual step by step charging of the output capacitor 6 is illustrated in FIG. 4. As appears from this figure the voltage of the output capacitor 6, $U_{out}$, approaches the voltage $U_{bat}$ asymptomatically. It should be noted that the capacitances of the capacitors 6 and 24 are equal in the example described in FIGS. 3 and 4.

To avoid the voltage on the output capacitor 6 exceeding a predetermined security level, a comparator (not shown) is provided to compare the output voltage with the predetermined security value. If this level is reached the charging is stopped.

For stimulation with a constant charge it is in practice sufficient to have a charge pump with a maximum output voltage of twice the stimulation output voltage. The amount of charge delivered to the output capacitor is then proportional to the operation time of the charge pump. The operation time of the charge pump after a stimulation is thus selected for getting the desired output stimulation charge, as the amount of charge in the output capacitor is linearly increasing with the charging time.

In terms of energy, an inductive charge storage means is better than a capacitive means because in a capacitive circuit 50% of the energy is lost in charging resistances. The use of inductances is not associated with any such losses. Charging losses will be reduced to a minimum and the efficiency will be high, about 90% or even more.

Figure 5:
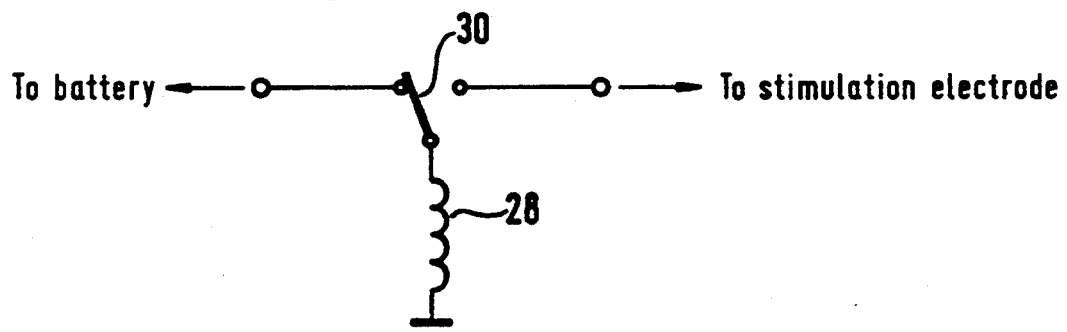
FIG. 5 shows a coil serving as a charge storage means.

In the embodiment shown in FIG. 5 an inductance in the form of a high inductance coil 28, preferably with a ferrite core, can be charged to a selected level by connection to the battery through a switch 30. The magnetic energy stored in the coil 28 is then discharged through the stimulation electrode as a stimulation pulse by switching the switch 30 to its second position.

The amount of charge stored in the coil 28 and transferred to the stimulation electrode is proportional to the time for which the coil 28 is connected to the battery. The current through the coil 28 is increasing approximately linearly with time, and with the charging voltage for short charging times. Alternatively for the charging of the coil 28 a fixed charging time and a variable charging voltage could be used.

When using an inductance as a charge storage means one needs only to check that necessary energy or charge is delivered from the coil for stimulation, and during this procedure the voltage may assume those values which are needed. Thus if the transition impedance between the electrode and tissue is increased, the voltage will be higher to maintain a sufficient current or the predetermined stimulation charge.

Figure 6:
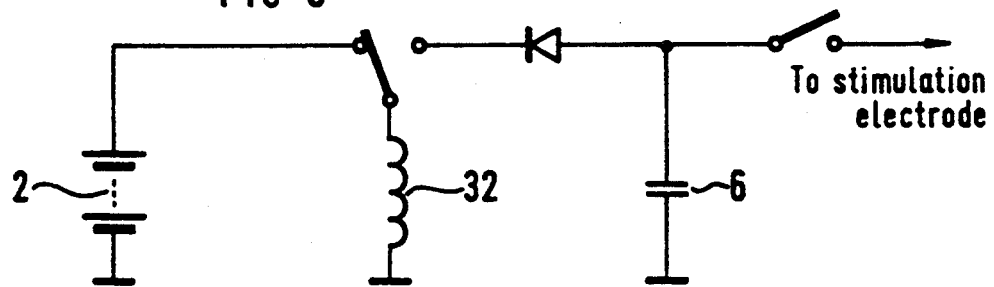
FIG. 6 shows an alternative to the charge pump of FIG. 3.

In FIG. 6 an alternative to the charge pump shown in FIG. 3 is illustrated wherein the capacitor 24 is replaced by a coil for charging the output capacitor 6. In this embodiment the inductance is not directly discharged for stimulation, but forms an output stage together with an output capacitor.

The coil 32 is thus charged from the battery 2 and the charge is then transferred to the capacitor 6 prior to stimulation. In this way an "inductive" charge pump analogous to the capacitive charge pump described in connection with FIGS. 3 and 4 is obtained. In this case a smaller coil can be used than if the coil is used as a charge storage means for direct stimulation as shown in FIG. 5. The capacitor 6 can be charged in a one step or in a multi-step procedure, the amount of charge transferred to the capacitor 6 being determined by the operation time of the circuit. If the coil 32 in a multi-step procedure is charged with a constant charge for each step the amount of charge transferred to the capacitor 6 will again be proportional to the number of charging steps (of the time of active operation of the circuit.

It is also possible to charge a plurality of coils connected in parallel to a charging source and then connect the charged coils in series and discharge them to a capacitor, which thus is charged to a voltage which can be considerably higher than the voltage of the charging source. In this way an inductive voltage multiplier analogous to the capacitive voltage multiplier described in connection with FIG. 2 is realized.

Although modifications and changes may be suggested by those skilled in the art, it is the intention of the inventors to embody within the patent warranted hereon all changes and modifications as reasonably and properly come within the scope of their contribution to the art.

I claim as my invention:

1. A cardiac pacemaker comprising:
   a stimulation electrode for in vivo delivery of a stimulation pulse to heart tissue;
   pulse source means for generating said stimulation pulse;
   said pulse source means including means for storing charge, charging means for charging said means for storing charge with a predetermined amount of charge for each stimulation pulse to be generated, and means for discharging said means for storing charge through said stimulation electrode to form a heart stimulation pulse; and
   said charging means comprising a battery, at least two capacitors, and circuitry means for connecting said capacitors in parallel across said battery for charging said capacitors and for connecting said capacitors in series and discharging the charge in said capacitors to said means for storing charge.

2. A cardiac pacemaker as claimed in claim 1 wherein said means for storing charge comprises an output capacitor.

3. A cardiac pacemaker as claimed in claim 2 further comprising comparator means for comparing a voltage across said output capacitor and for controlling said means for charging to stop charging of said output capacitor when said voltage across said output capacitor reaches a predetermined level.

4. A cardiac pacemaker as claimed in claim 1 wherein said means for storing charge comprises a high-inductance coil.

5. A cardiac pacemaker as claimed in claim 4 further comprising means for controlling said means for charging for fixing a time of charging of said high-inductance coil to a predetermined length.

6. A cardiac pacemaker comprising:
   a stimulation electrode for in vivo delivery of a stimulation pulse to heart tissue; pulse source means for generating said stimulation pulse;
   said pulse source means including means for storing charge, charging means for charging said means for storing charge with a predetermined amount of charge for each stimulation pulse to be generated, and means for discharging said means for storing charge through said stimulation electrode to form a heart stimulation pulse; and
   said charging means comprising a battery and a coil connected between said battery and said means for storing charge, and circuit means for initially connecting said coil to said battery for developing charge in said coil and for subsequently disconnecting said coil from said battery and connecting said coil to said means for storing charge to deliver the charge in said coil to said means for storing charge.

7. A cardiac pacemaker as claimed in claim 6 wherein said circuit means includes switch means for alternatingly connecting said coil to said battery while disconnecting said coil from said means for storing charge and then disconnecting said coil from said battery and connecting said coil to said means for storing charge for delivering said charge from said coil to said means for storing charge in steps.

8. A cardiac pacemaker as claimed in claim 6 wherein said circuit means includes means for fixing a time for connecting said coil to said battery to a predetermined length.

* * * * *